(12) United States Patent
Campbell et al.

(10) Patent No.: US 10,662,299 B2
(45) Date of Patent: May 26, 2020

(54) HEAT GENERATING MICROCAPSULES FOR SELF-HEALING POLYMER APPLICATIONS

(71) Applicant: International Business Machines Corporation, Armonk, NY (US)

(72) Inventors: Eric J. Campbell, Rochester, MN (US); Sarah K. Czaplewski, Rochester, MN (US); Joseph Kuczynski, North Port, FL (US); Timothy J. Tofil, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 109 days.

(21) Appl. No.: 15/618,589

(22) Filed: Jun. 9, 2017

(65) Prior Publication Data

US 2018/0355126 A1 Dec. 13, 2018

(51) Int. Cl.
| | | |
|---|---|---|
| *C08K 9/10* | (2006.01) | |
| *C08J 3/24* | (2006.01) | |
| *C08J 3/00* | (2006.01) | |
| *B01J 13/04* | (2006.01) | |
| *B01J 13/22* | (2006.01) | |
| *B29C 73/22* | (2006.01) | |
| *B01J 13/06* | (2006.01) | |
| *A61K 9/50* | (2006.01) | |
| *C08K 5/14* | (2006.01) | |

(52) U.S. Cl.
CPC ............ *C08J 3/241* (2013.01); *B01J 13/04* (2013.01); *B01J 13/06* (2013.01); *B01J 13/22* (2013.01); *B29C 73/22* (2013.01); *C08J 3/00* (2013.01); *C08K 9/10* (2013.01); *A61K 9/5094* (2013.01); *C08K 5/14* (2013.01)

(58) Field of Classification Search
CPC .. B01J 13/02; C08J 3/241; C08K 9/10; B29C 73/22; H05K 1/0353; H05K 1/0201
See application file for complete search history.

(56) References Cited

U.S. PATENT DOCUMENTS

| | | | |
|---|---|---|---|
| 4,816,367 A | 3/1989 | Sakojiri et al. | |
| 5,508,893 A | 4/1996 | Nowak et al. | |
| 6,833,191 B2 | 12/2004 | Bayless | |
| 6,876,143 B2 | 4/2005 | Daniels | |
| 7,806,072 B2 | 10/2010 | Hamilton, II et al. | |
| 8,137,597 B1 | 3/2012 | Brott et al. | |
| 9,217,736 B2 | 12/2015 | Ribi | |
| 9,307,692 B2 | 4/2016 | Boday et al. | |
| 9,856,404 B2 | 1/2018 | Campbell et al. | |
| 9,896,389 B2 | 2/2018 | Campbell et al. | |
| 2007/0021533 A1* | 1/2007 | Yan et al. | C08K 9/10 523/200 |
| 2007/0054762 A1 | 3/2007 | Tocco | |
| 2009/0036568 A1 | 2/2009 | Merle et al. | |
| 2012/0077279 A1 | 3/2012 | Wiesner et al. | |
| 2014/0371362 A1 | 12/2014 | Wilson | |
| 2015/0166822 A1 | 6/2015 | Samsudin et al. | |
| 2015/0364710 A1 | 12/2015 | Chen et al. | |
| 2016/0289484 A1 | 10/2016 | Lalgudi et al. | |
| 2017/0027197 A1 | 2/2017 | Bourke, Jr. et al. | |
| 2017/0129825 A1 | 5/2017 | Campbell et al. | |
| 2018/0340032 A1 | 11/2018 | Campbell et al. | |

OTHER PUBLICATIONS

Wilson et al., *Evaluation of Peroxide Initiators for Radical Polymerization-Based Self-Healing Application*, Journal of Polymer Science Part A: Polymer Chemistry, Jun. 15, 2010, pp. 2698-2708, vol. 48, Issue 12, Wiley Periodicals, Inc., Hoboken, New Jersey.
Akzonobel, *Product Search—AkzoNobel Polymer Chemistry*, akzonobel.com (online), accessed Mar. 1, 2017, 4 pp., <https://www.akzonobel.com/polymer/our_products/product_search/?pgid=17&appid=0&pformid=&pycactiyityid=&Idpeactiyityid=&stid=&ctype=&cat=>.
AUS920170094US1, Appendix P; List of IBM Patent or Applications Treated as Related, dated Sep. 12, 2017, 2 pages.
U.S. Appl. No. 15/590,676, to Eric J. Campbell et al., entitled, *Light Emitting Shell in Shell Microcapsules*, filed May 9, 2017, assigned to International Business Machines Corporation.
Yamaura et al., *Preparation and characterization of (3-aminopropyl) triethoxysilane-coated magnetite nanoparticles*, Journal of Magnetism and Magnetic Materials, vol. 279, Issues 2-3, Aug. 2004, pp. 210-217, ScienceDirect.com (online), Elsevier B.V., Amsterdam.
Kreft et al., *Shell-in-Shell Microcapsules: A Novel Tool for Integrated, Spatially Confined Enzymatic Reactions*, Angewandte Chemie, Int. Ed., Jul. 2007 (online Jun. 2007), vol. 46, Issue 29, pp. 5605-5608, Wiley-VCH Verlag GmbH & Co., KGaA, Weinheim, DOI: 10.1002/anie.200701173.
Xiong et al., *Towards Theranostic Multicompartment Microcapsules: in-situ Diagnostics and Laser-induced Treatment*, Theranostics, vol. 3, Issue 3, Feb. 2013, pp. 141-151, Ivyspring International, Sydney, Australia.
Parakhonskiy, *Colloidal micro- and nano-particles as templates for polyelectrolyte multilayer capsules*, Advances in Colloid and Interface Science, May 2014, vol. 207, pp. 253-264, ScienceDirect.com (online), Elsevier B.V., Amsterdam.

* cited by examiner

Primary Examiner — Nathan M Nutter
(74) Attorney, Agent, or Firm — Peter Edwards (57) ABSTRACT

A self-healing polymeric material includes a polymeric matrix material, a plurality of monomer mixture microcapsules dispersed in the polymeric matrix material, and a plurality of heat generating microcapsules dispersed in the polymeric matrix material. Each monomer mixture microcapsule of the plurality of monomer mixture microcapsules encapsulates a mixture of materials that includes a monomer and a heat-triggered initiator. Each heat generating microcapsule of the plurality of heat generating microcapsules encapsulates multiple reactants that undergo an exothermic chemical reaction. The exothermic chemical reaction generates sufficient heat to cause the heat-triggered initiator to initiate a polymerization reaction.

7 Claims, 7 Drawing Sheets

HEAT GENERATING MICROCAPSULES FOR SELF-HEALING POLYMER APPLICATIONS

BACKGROUND

Typical self-healing polymers utilize encapsulated monomers that react in the presence of a catalyst that is incorporated into the polymer matrix. The healing material is limited in selection because a proper monomer/catalyst pair must be compatible with the polymer matrix. Additionally, self-healing schemes typically involve thermally initiated reactions. In some cases (e.g., outdoor applications with low ambient temperatures), such thermally initiated reactions may proceed too slowly to repair damage at an early stage. Accordingly, in such cases, an external heat source may be utilized to accelerate the reaction in order to prevent further propagation of the damage.

SUMMARY

According to an embodiment, a self-healing polymeric material is disclosed. The self-healing polymeric material includes a polymeric matrix material, a plurality of monomer mixture microcapsules dispersed in the polymeric matrix material, and a plurality of heat generating microcapsules dispersed in the polymeric matrix material. Each monomer mixture microcapsule of the plurality of monomer mixture microcapsules encapsulates a mixture of materials that includes a monomer and a heat-triggered initiator. Each heat generating microcapsule of the plurality of heat generating microcapsules encapsulates multiple reactants that undergo an exothermic chemical reaction. The exothermic chemical reaction generates sufficient heat to cause the heat-triggered initiator to initiate a polymerization reaction.

According to another embodiment, a process of utilizing a heat generating microcapsule for polymeric self-healing is disclosed. The process includes dispersing a monomer mixture microcapsule in a polymeric matrix material. The monomer mixture microcapsule encapsulates a mixture of materials that includes a monomer and a heat-triggered initiator. The process also includes dispersing a heat generating microcapsule in the polymeric matrix material. The heat generating microcapsule encapsulates multiple reactants that undergo an exothermic chemical reaction that generates sufficient heat to cause the heat-triggered initiator to initiate a polymerization reaction. The monomer mixture microcapsule is adapted to rupture to cause migration of the mixture of materials into a crack in the polymeric matrix material, and the heat generating microcapsule is adapted to cause the multiple reactants to undergo the exothermic chemical reaction within the heat generating microcapsule in response to application of a compressive force.

According to another embodiment, an in-situ heat generation process is disclosed that includes forming an article of manufacture that includes a self-healing polymeric material. The self-healing polymeric material includes a polymeric matrix material, a plurality of monomer mixture microcapsules dispersed in the polymeric matrix material, and a plurality of heat generating microcapsules dispersed in the polymeric matrix material. Each of the monomer mixture microcapsules encapsulates a mixture of materials that includes a monomer and a heat-triggered initiator. Each of the heat generating microcapsules encapsulates multiple reactants that undergo an exothermic chemical reaction. The in-situ heat generation process also includes exposing the article of manufacture to an environment that results in formation of a crack in the polymeric matrix material. The crack causes microcapsule rupture of a monomer mixture microcapsule, which results in migration of the mixture of materials into the crack. Without applying an external heat source to the article of manufacture, the exothermic chemical reaction within the heat generating microcapsule generates sufficient heat to cause the heat-triggered initiator to initiate a polymerization reaction to form a cross-linked material that seals the crack.

The foregoing and other objects, features and advantages of the invention will be apparent from the following more particular descriptions of exemplary embodiments of the invention as illustrated in the accompanying drawings wherein like reference numbers generally represent like parts of exemplary embodiments of the invention.

DETAILED DESCRIPTION

The present disclosure describes heat generating microcapsules and processes of utilizing the heat generating microcapsules for in-situ generation of heat for self-healing polymeric applications. In the present disclosure, a heat generating microcapsule includes multiple compartments to isolate a first reactant (or a first set of reactants) from a second reactant (or a second set of reactants) within the same heat generating microcapsule. Application of a particular stimulus (e.g., a compressive force) to the heat generating microcapsule results in rupture of an inner compartment, enabling the first reactant(s) and the second reactant(s) to mix and undergo an exothermic chemical reaction within the heat generating microcapsule.

The heat generating microcapsules of the present disclosure may be dispersed within a self-healing polymeric matrix material to enable thermal energy to be generated in situ within the self-healing polymeric matrix material. The self-healing polymeric matrix material further includes a second set of microcapsules (also referred to herein as "monomer mixture microcapsules") encapsulating a monomer mixture that includes monomers and a heat-triggered initiator (and optionally an activator). In some embodiments, the monomer mixture microcapsules may include monomers that undergo a free-radical-initiated polymerization reaction, and the heat-triggered initiator may correspond to a peroxide initiator that thermally decomposes at an elevated temperature (with respect to an ambient temperature) to trigger the free-radical-initiated polymerization of the monomers.

Propagation of a crack in the self-healing polymeric matrix material results in rupture of a monomer mixture microcapsule (or multiple microcapsules), causing the monomer mixture (including the heat-triggered initiator) to fill the crack. Further propagation of the crack results in application of a compressive force to a heat generating microcapsule (or multiple heat generating microcapsules), triggering the exothermic chemical reaction within the heat generating microcapsule. The exothermic chemical reaction may generate sufficient heat to trigger thermal decomposition of the heat-triggered initiator, resulting in a polymerization reaction (e.g., a free-radical-initiated polymerization reaction) of the monomer mixture that has filled the crack. The polymerization reaction proceeds at a rate that is sufficient to enable the crack to be repaired at an early stage, regardless of the ambient temperature. Accordingly, the heat generating microcapsules of the present disclosure may be particularly useful in outdoor applications where the ambient temperature may provide insufficient heat to trigger a thermally-initiated reaction.

As used herein, the term "microcapsule" is used to refer to capsules that are in a range of about 10 microns to 1000 microns in diameter. However, it will be appreciated that the following disclosure may be applied to capsules having a smaller size (also referred to as "nanocapsules").

Figure 1:
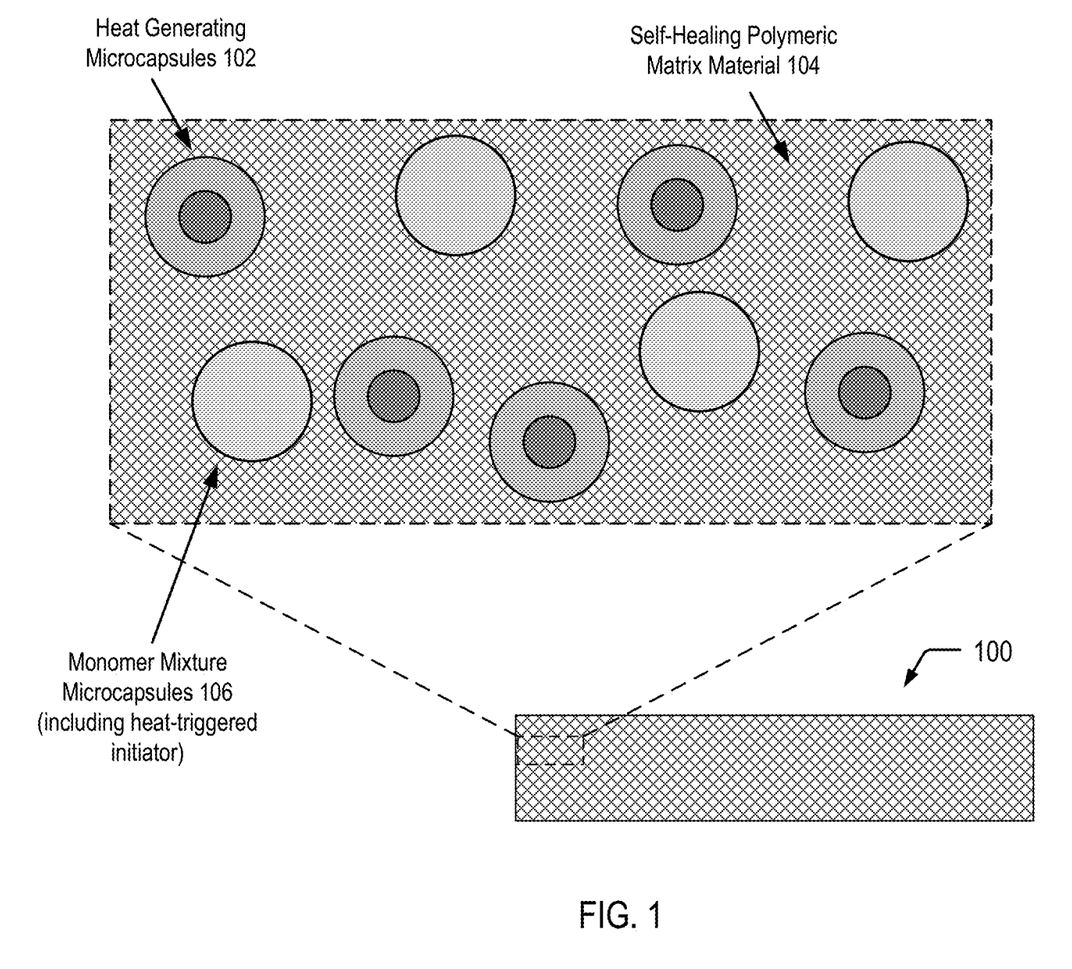
FIG. 1 is a cross-sectional view of selected portions of an article of manufacture that utilizes heat generating microcapsules for polymeric self-healing, according to one embodiment.

FIG. 1 illustrates a cross-sectional view of selected portions of an article of manufacture 100 that utilizes heat generating microcapsules 102 for polymeric self-healing, according to one embodiment. In FIG. 1, a self-healing polymeric matrix material 104 includes a plurality of the heat generating microcapsules 102 and a plurality of monomer mixture microcapsules 106 dispersed therein. The monomer mixture microcapsules 106 may encapsulate a mixture of materials that undergo a polymerization reaction (e.g., free-radical-initiated polymerization reaction). To illustrate, the mixture may include a heat-triggered initiator (e.g., a free-radical initiator), such as a peroxide initiator, that thermally decomposes at an elevated temperature (with respect to an ambient temperature) to trigger the free-radical-initiated polymerization reaction. As illustrated and further described herein with respect to FIGS. 3A-3C, propagation of a crack in the self-healing polymeric matrix material 104 may result in rupture of at least one of the monomer mixture microcapsules 106, causing the encapsulated mixture (including the heat-triggered initiator) to fill the crack. Further propagation of the crack results in application of a compressive force to at least one of the heat generating microcapsules 102, triggering an exothermic chemical reaction within at least one of the heat generating microcapsules 102. The exothermic chemical reaction may generate sufficient heat to trigger the thermal decomposition of the free-radical initiator, resulting in a free-radical-initiated polymerization reaction of the mixture to "heal" the self-healing polymeric matrix material 104 by forming a cross-linked material that seals the crack.

The monomer mixture microcapsules 106 encapsulate a mixture of materials that includes at least a monomer and a polymerization initiator. In some cases, the mixture may further include an activator. As an illustrative, non-limiting example, the monomer may include an epoxy-based material, such as an epoxy vinyl ester (EVE) resin. In a particular embodiment, the peroxide initiator may correspond to lauroyl peroxide, which exhibits an onset of decomposition at a temperature of about 86° C. (also referred to herein as an "Onset T"). Other examples of peroxide initiators may include benzoyl peroxide (Onset T of about 109° C.), methyl ethyl ketone peroxide (Onset T of about 128° C.), or tent-butyl peroxybenzoate (Onset T of about 112° C.), among other alternatives. Examples of activators may include N,N-dimethyl aniline, 4,N,N-trimethylaniline, or 4,4'-methylene bis(N,N-dimethyl aniline), among other alternatives. One of ordinary skill in the art will appreciate that other peroxide initiators or a combination of initiators, such as those available from Akzo Nobel N.V., may also represent suitable heat-triggered initiators for the polymeric self-healing applications described herein (e.g., for outdoor applications at sub-ambient temperatures).

In FIG. 1, the monomer mixture microcapsules 106 are shown prior to the formation of a crack in the self-healing polymeric matrix material 104 that results in rupture of at least one of the monomer mixture microcapsules 106, causing the encapsulated mixture to fill the crack. As illustrated and further described herein with respect to FIGS. 3A and 3B, a crack in the self-healing polymeric matrix material 104 may result in the rupture of one (or more) of the monomer mixture microcapsules 106 and the release of the encapsulated monomer mixture into the crack. As illustrated and further described herein with respect to FIG. 3C, the heat generated by the exothermic chemical reaction within one (or more) of the heat generating microcapsules 102 may be sufficient to cause the heat-triggered initiator (e.g., a free-radical initiator) to initiate a polymerization reaction (e.g., a free-radical-initiated polymerization reaction) to form a cross-linked material that seals the crack, thereby preventing further propagation of the crack.

The heat generating microcapsules 102 illustrated in FIG. 1 include multiple compartments and are also referred to herein as multiple-compartment microcapsules. In FIG. 1, the heat generating microcapsules 102 are shown prior to application of a compressive force that results in an exothermic chemical reaction within the individual heat generating microcapsules 102. Accordingly, FIG. 1 illustrates that the compartments of the heat generating microcapsules 102 enable isolation of reactants in order to prevent the exothermic reaction prior to application of the compressive force.

In the particular embodiment depicted in FIG. 1, the heat generating microcapsules 102 dispersed in the self-healing polymeric matrix material 104 have a shell-in-shell architecture with an inner shell contained within an outer shell, where the inner shell is adapted to rupture in response to application of a compressive force in order to trigger an exothermic chemical reaction within the heat generating microcapsules 102. Thus, the individual heat generating microcapsules 102 depicted in FIG. 1 may correspond to the multiple-compartment microcapsule (having a shell-in-shell architecture) formed according to the process described herein with respect to FIG. 4. It will be appreciated that, in alternative embodiments, the heat generating microcapsules 102 may have an alternative multiple-compartment microcapsule design, may include more than one type of multiple-compartment microcapsule design, or a combination thereof.

Thus, FIG. 1 illustrates an example of an article of manufacture that includes heat generating microcapsules dispersed in a polymeric matrix material to enable self-healing of the polymeric matrix material. As illustrated and further described herein with respect to FIGS. 3A-3C, propagation of a crack in the polymeric matrix material causes the monomer mixture microcapsule(s) to rupture and release the encapsulated mixture (including the heat-triggered initiator) into the crack. Further propagation of the crack results in application of a compressive force to the heat generating microcapsule(s) that triggers an exothermic chemical reaction within the heat generating microcapsule(s). The exothermic chemical reaction generates sufficient heat to cause the heat-triggered initiator to initiate the polymerization reaction, thereby "healing" the polymeric matrix material by forming a cross-linked material that seals the crack to prevent further propagation of the crack.

Figure 2A:
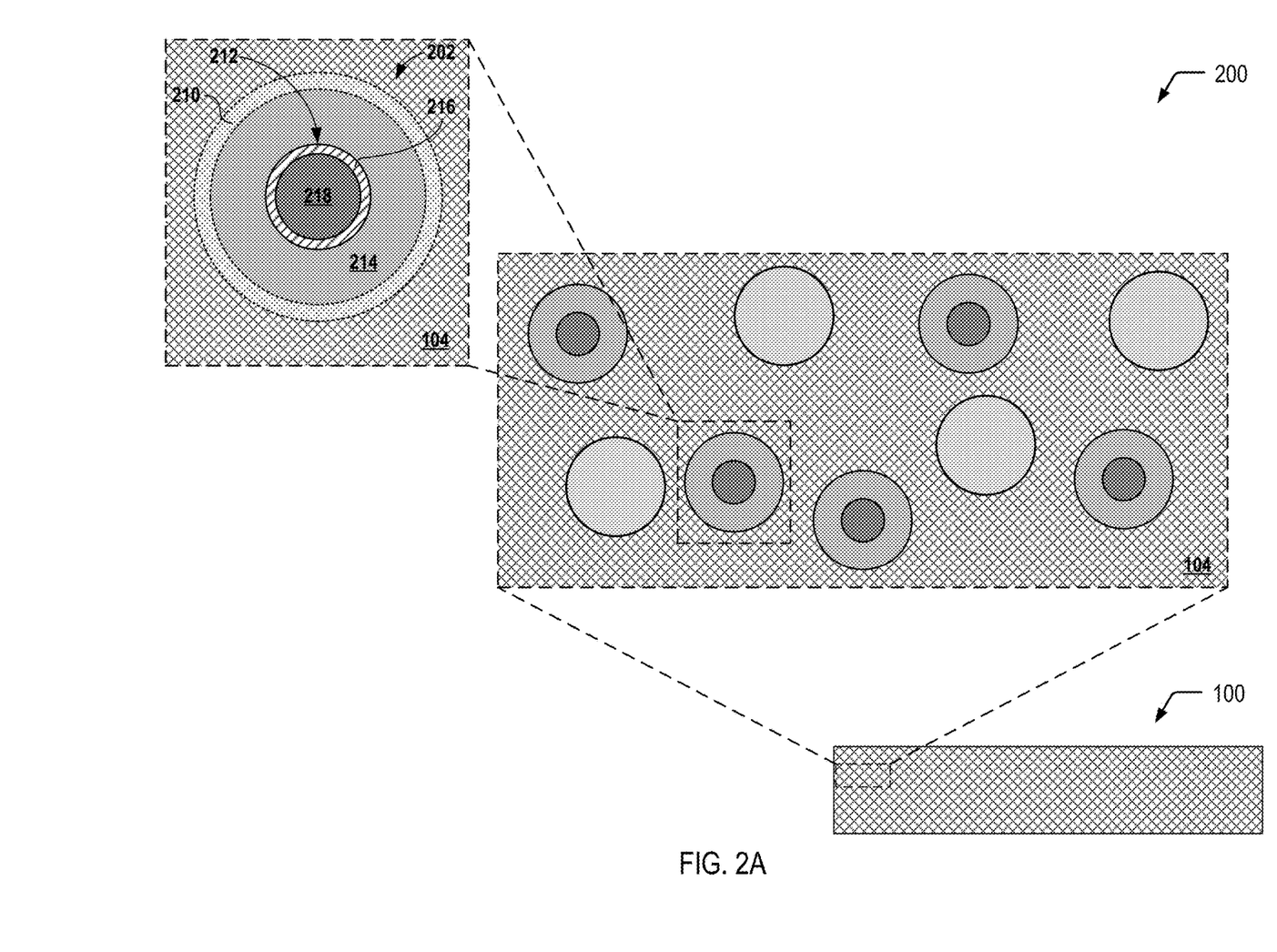
FIG. 2A is a cross-sectional view of a multiple-compartment microcapsule corresponding to one of the heat generating microcapsules depicted in FIG. 1, in which reactants that undergo an exothermic reaction are isolated within individual compartments of the multiple-compartment microcapsule, according to one embodiment.

FIG. 2A illustrates an exploded cross-sectional view 200 of a multiple-compartment microcapsule 202 corresponding to one of the plurality of the heat generating microcapsules 102 depicted in FIG. 1. In FIG. 2A, reactants that undergo an exothermic chemical reaction are isolated within individual compartments of the multiple-compartment microcapsule 202. As illustrated and further described herein with respect to FIG. 2B, application of a compressive force to the multiple-compartment microcapsule 202 (e.g., as a result of a crack in the self-healing polymeric matrix material 104) enables the isolated reactants to mix and undergo the exothermic chemical reaction within the multiple-compartment microcapsule 202.

The exploded cross-sectional view 200 of FIG. 2A illustrates that the multiple-compartment microcapsule 202 has an outer wall 210 (also referred to herein as the "outer shell") and contains an inner microcapsule 212 and a first reactant 214 (or a first set of multiple reactants). The inner microcapsule 212 has a capsule wall 216 (also referred to herein as the "inner shell") and contains a second reactant 218 (or a second set of multiple reactants). The first reactant(s) 214 within the microcapsule 202 may surround the inner microcapsule 212, and the first reactant(s) 214 may be prevented from contacting the second reactant(s) 218 by the capsule wall 216 of the inner microcapsule 212. In a particular embodiment, the capsule wall 216 of the inner microcapsule 212 may be formed to rupture under a particular compressive force, and the outer wall 210 of the microcapsule 202 may be formed so as to not rupture under that compressive force.

Figure 3A:
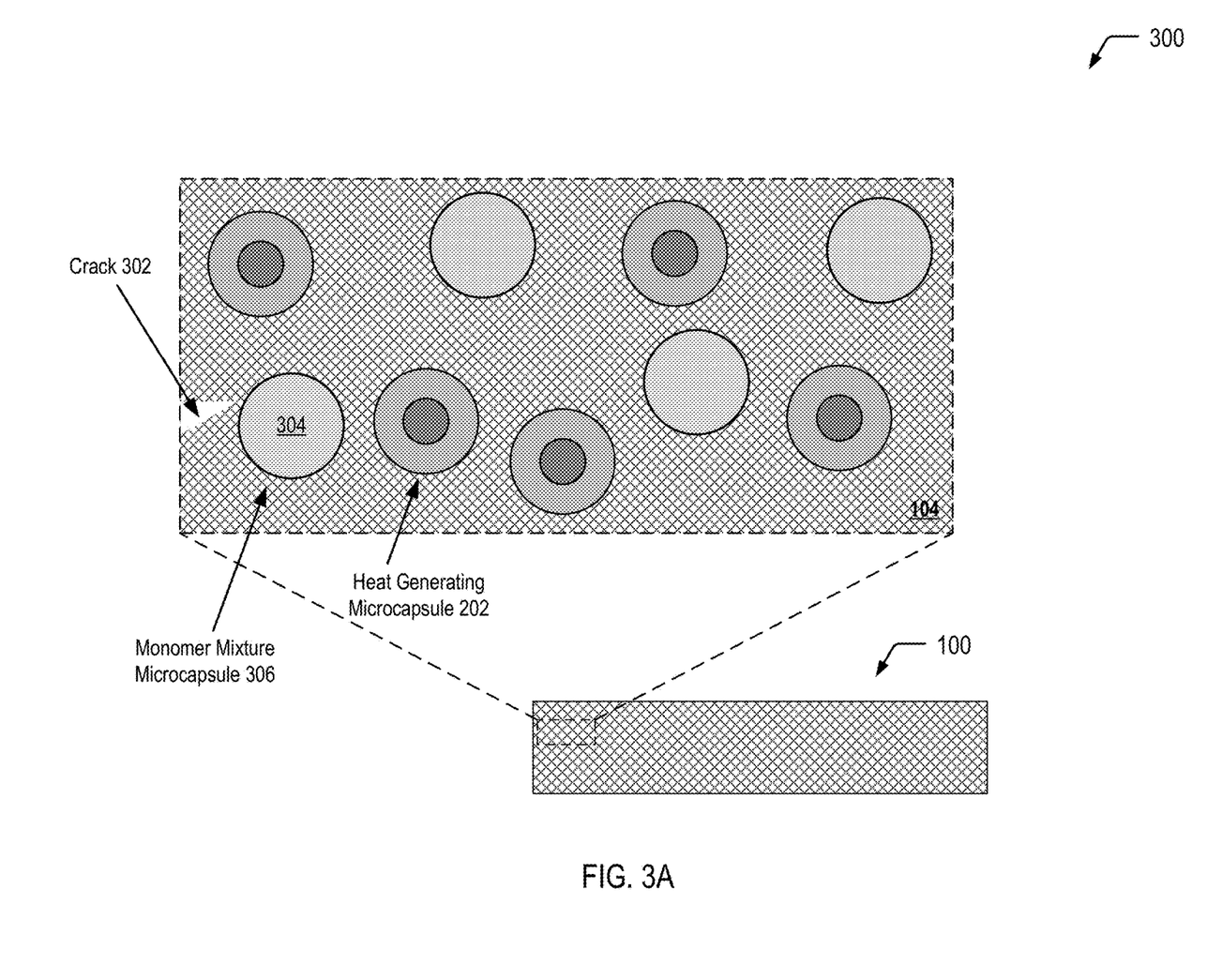
FIG. 3A is a cross-sectional view of selected portions of the article of manufacture of FIG. 1 at a first stage of propagation of a crack in the self-healing polymeric matrix material, according to one embodiment.
Figure 3B:
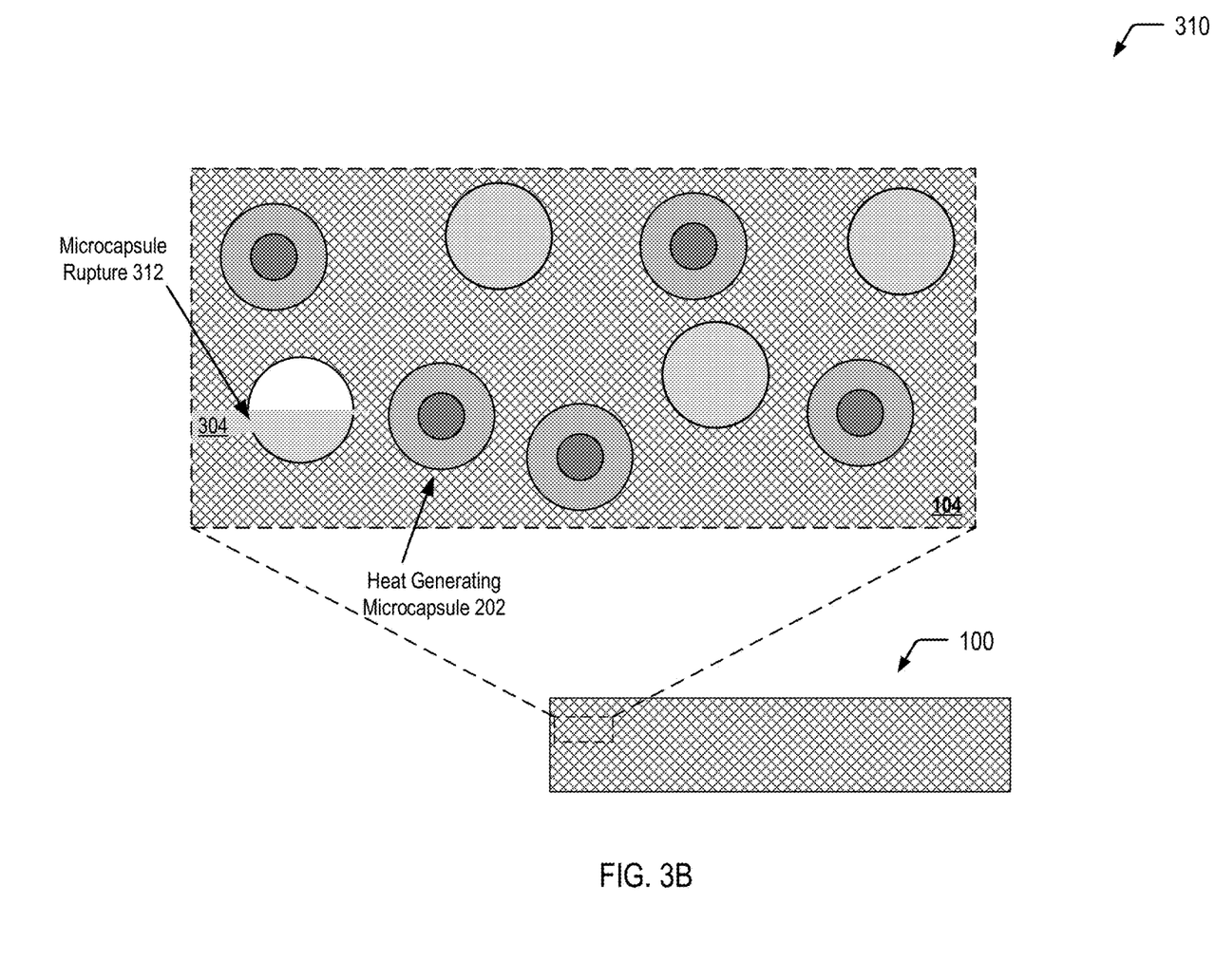
FIG. 3B is a cross-sectional view of selected portions of the article of manufacture of FIG. 1 at a second stage of propagation of the crack resulting in rupture of a heat-curable sealant microcapsule and release of heat-curable sealant to fill the crack, according to one embodiment.

As illustrated and further described herein with respect to FIG. 3B, a crack in the self-healing polymeric matrix material 104 may result in rupture of the capsule wall 216 of the inner microcapsule 212, allowing the first reactant(s) 214 and the second reactant(s) 218 to mix and undergo an exothermic chemical reaction. In a particular embodiment, the first reactant(s) 214 may correspond to hydrogen peroxide, and the second reactant(s) 218 may correspond to a mixture of iron powder and ferric nitrate (or another catalytic material).

In some embodiments, the multiple-compartment microcapsule 202 may have a diameter of less than 5.0 microns, or the multiple-compartment microcapsule 202 may have a smaller diameter of less than 2.0 microns. A ratio of 0.2 percent of such microcapsules 202 per unit mass of the self-healing polymeric matrix material 104 (having the monomer mixture microcapsules 106 dispersed therein) may produce a temperature increase of at least 1.04° C. per gram of the self-healing polymeric matrix material 104 (having the monomer mixture microcapsules 106 dispersed therein).

In FIG. 2A, the multiple-compartment microcapsule 202 is shown prior to application of a compressive force to the multiple-compartment microcapsule 202. Accordingly, the compartment(s) of the microcapsule isolate reactants that undergo an exothermic chemical reaction when mixed. As described further herein with respect to FIG. 3C, a crack in the self-healing polymeric matrix material 104 results in rupture of the capsule wall 216 of the inner microcapsule 212, allowing the reactants to mix and undergo the exothermic chemical reaction.

Figure 2B:
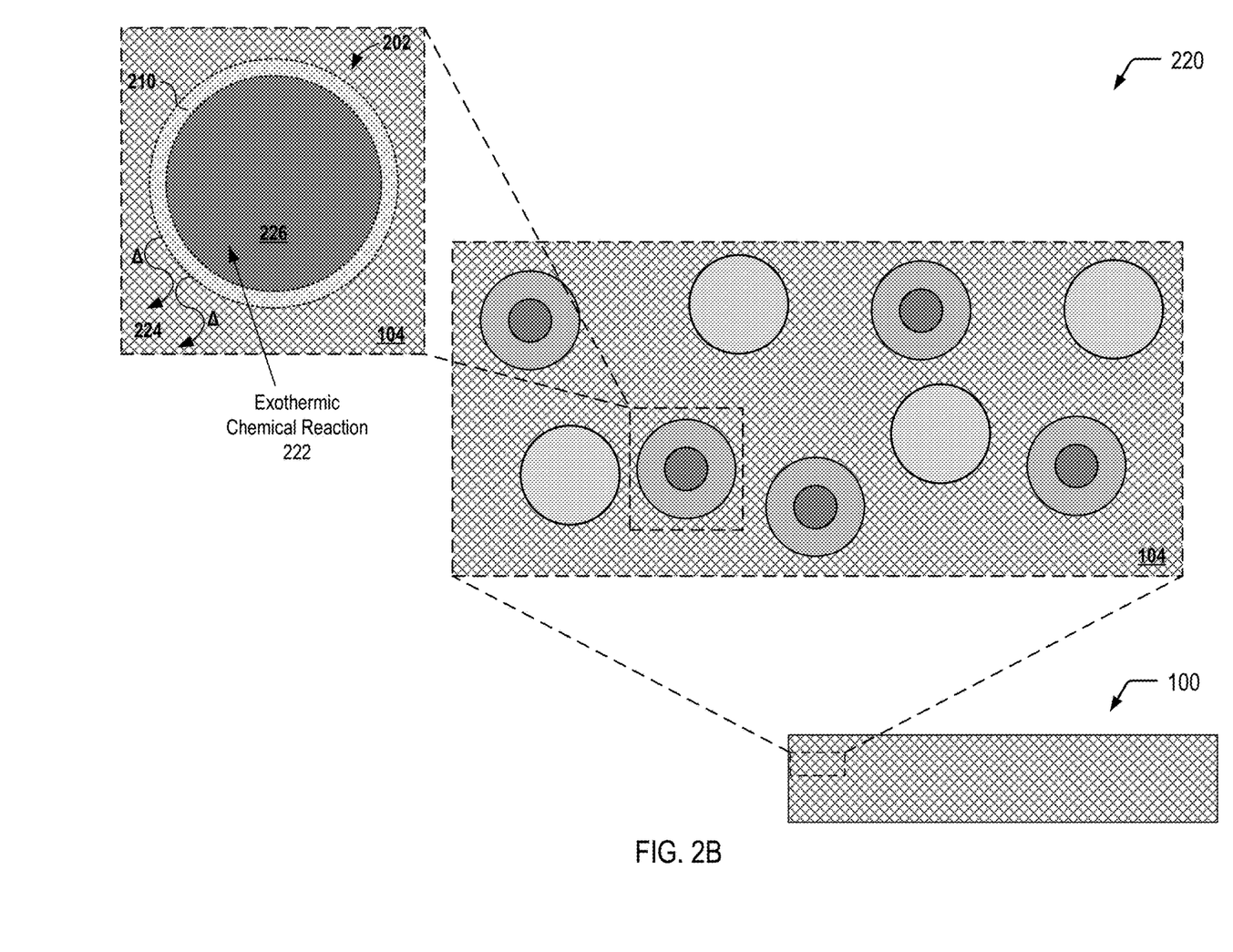
FIG. 2B is a cross-sectional view of the multiple-compartment microcapsule of FIG. 2A after a compressive force results in rupture of an inner compartment of the microcapsule to enable the reactants to undergo the exothermic chemical reaction within the microcapsule, according to one embodiment.

FIG. 2B illustrates an exploded cross-sectional view 220 of the individual multiple-compartment microcapsule 202 of FIG. 2A after application of a compressive force to the multiple-compartment microcapsule 202. FIG. 2B illustrates that compression of the multiple-compartment microcapsule 202 results in rupture of the capsule wall 216 of the inner microcapsule 212 depicted in FIG. 2A to allow the first reactant(s) 214 and the second reactant(s) 218 to mix and undergo an exothermic chemical reaction 222. FIG. 2B further illustrates that, in some embodiments, application of the compressive force does not result in rupture of the outer wall 210 of the multiple-compartment microcapsule 202.

Figure 3C:
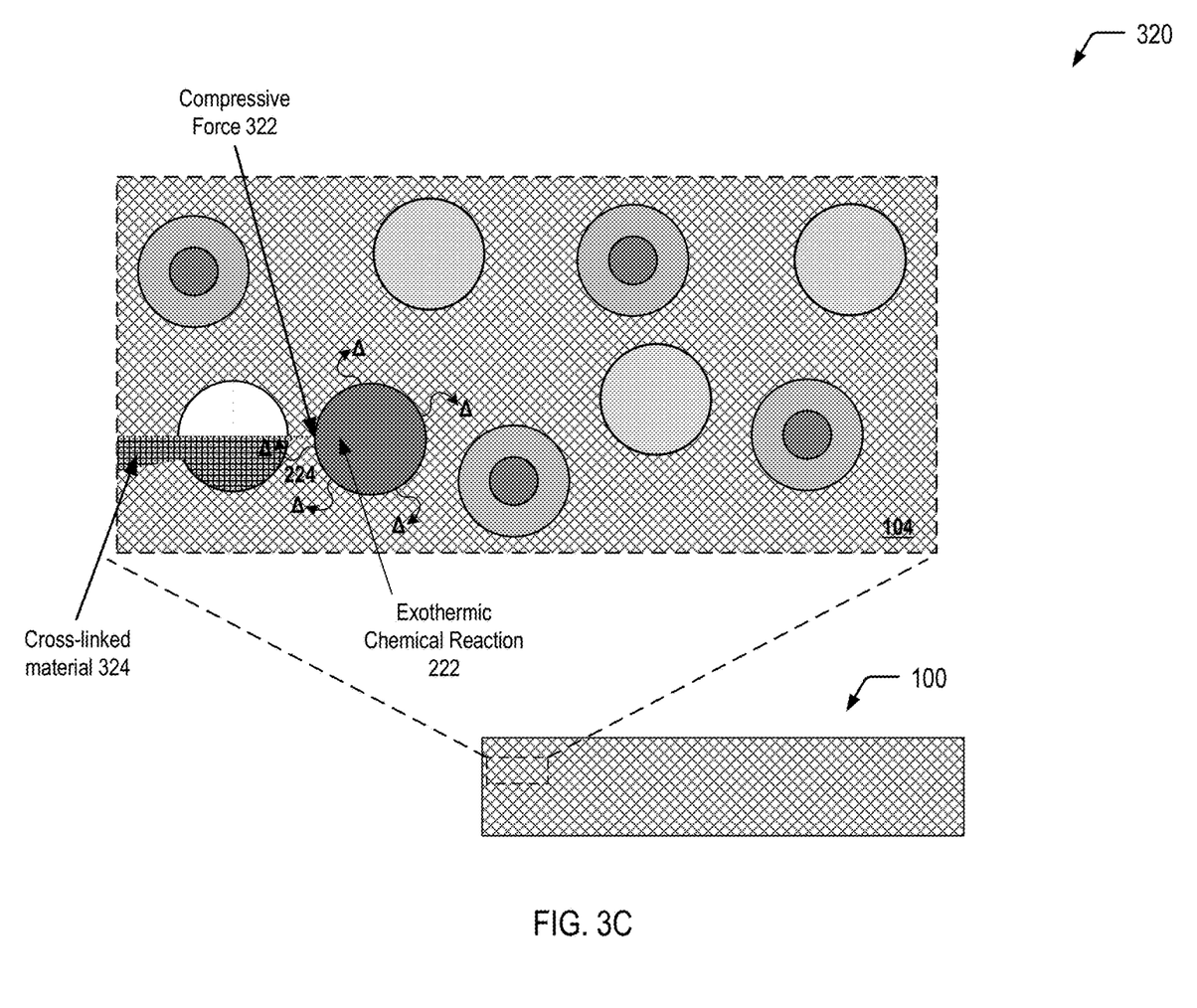
FIG. 3C is a cross-sectional view of selected portions of the article of manufacture of FIG. 1 at a third stage of propagation of the crack causing a compressive force to a heat generating microcapsule resulting in an exothermic chemical reaction that generates sufficient heat to cure the heat-curable sealant to seal the crack, according to one embodiment.

FIG. 2B illustrates that the exothermic chemical reaction 222 that occurs within the microcapsule 202 generates heat 224 (identified as "Δ" in FIG. 2B) that is transferred through the outer shell 210 into the surrounding self-healing polymeric matrix material 104. The heat 224 may be sufficient to polymerize the monomer mixture 304 that fills the crack 302 (as shown in FIGS. 3A and 3B) in order to "heal" the crack 302 by forming the cross-linked material 324 (as shown in FIG. 3C) and preventing further propagation of the crack 302.

FIG. 2B further illustrates that the multiple-compartment microcapsule 202 may contain a reaction product 226 of the reaction of the first reactant(s) 214 and the second reactant(s) 218 (as shown in FIG. 2A). As the outer wall 210 may remain intact after application of the particular compressive force, the outer wall 210 may prevent the reaction product 226 from contacting the self-healing polymeric matrix material 104.

In a particular embodiment, the exothermic chemical reaction 222 that occurs within the multiple-compartment microcapsule 202 corresponds to a reaction between an oxidizing agent (e.g., oxygen) and a reducing agent (e.g., iron), according to the reaction equation:

4 Fe(s)+3 $O_2$(g)===>2 $Fe_2O_3$(s) Hrxn=−1.65103 kJ

According to the reaction equation, 4 moles of iron react with 3 moles of oxygen, such that in an embodiment iron may comprise 53% of the combined mass of the two reactants and oxygen may comprise 43% of that combined mass. In a particular embodiment, the multiple-compartment microcapsule 202 may contain iron powder and hydrogen peroxide. The iron powder may be mixed with a catalyst such as ferric nitrate, which when in contact with the hydrogen peroxide, liberates oxygen to react exothermically with the iron powder. For example, the multiple-compartment microcapsule 202 may use 1.5 moles of hydrogen peroxide per mole of iron, for example 0.56 grams of iron powder to 0.51 grams of hydrogen peroxide. The catalytic amount of ferric nitrate may be selected to achieve a desired reaction rate of heating, in kilojoules per second. For example, between 0.001 and 0.005 gram equivalents of ferric nitrate per liter of hydrogen peroxide results in a reaction rate producing heat at between 100 and 500 kilojoules per second.

In a particular embodiment, the multiple-compartment microcapsule 202 may contain a mixture of iron powder and ferric nitrate in the inner microcapsule 212 as the second reactant(s) 218 and may contain hydrogen peroxide as the first reactant(s) 214 surrounding the inner microcapsule 212. In some embodiments, the multiple-compartment microcapsule 202 may have a diameter of less than 5.0 microns, or the multiple-compartment microcapsule 202 may have a diameter of less than 2.0 microns.

Thus, FIGS. 2A and 2B illustrate an example of a heat generating microcapsule of the present disclosure before application of a compressive force (FIG. 2A) and after the application of the compressive force (FIG. 2B). As described further herein, the exothermic chemical reaction within the heat generating microcapsule may generate an amount of heat that is sufficient to cause the heat-triggered initiator to initiate a polymerization reaction of a monomer mixture 304 (see FIGS. 3A and 3B) that fills a crack 302 in the self-healing polymeric matrix material 104.

FIG. 3A illustrates a cross-sectional view 300 of selected portions of the article of manufacture 100 of FIG. 1 at a first stage of propagation of a crack 302 in the self-healing polymeric matrix material 104. In FIG. 3A, a monomer mixture 304 is shown as being encapsulated within an individual monomer mixture microcapsule 306 of the plurality of monomer mixture microcapsules 106 depicted in FIG. 1. Thus, the first stage of propagation of the crack 302 depicted in FIG. 3A shows the encapsulation of the monomer mixture 304 prior to rupture of the individual monomer mixture microcapsule 306.

FIG. 3B illustrates a cross-sectional view 310 of selected portions of the article of manufacture 100 of FIG. 1 at a second stage of propagation of the crack 302, resulting in microcapsule rupture 312 of the individual monomer mixture microcapsule 306 depicted in FIG. 3A. FIG. 3B further illustrates that the microcapsule rupture 312 enables the monomer mixture 304 to fill the crack 302. Thus, the second stage of propagation of the crack 302 depicted in FIG. 3B shows the monomer mixture 304 filling the crack 302 prior to rupture of the individual heat generating microcapsule 202.

FIG. 3C illustrates a cross-sectional view 320 of selected portions of the article of manufacture 100 of FIG. 1 at a third stage of propagation of the crack 302, resulting in application of a compressive force 322 to the individual heat generating microcapsule 202 of the plurality of heat generating microcapsules 102 dispersed in the self-healing polymeric matrix material 104. The compressive force 322 triggers the exothermic chemical reaction 222 within the heat generating microcapsule 202, generating sufficient heat to "seal" the crack 302 by initiating polymerization of the monomer mixture 304 in the crack 302 to form a cross-linked material 324 in the crack 302, thereby preventing further propagation of the crack 302.

One of ordinary skill in the art will appreciate that the self-healing polymeric matrix material 104 may include a sufficient amount of heat generating microcapsules 102 to generate an amount of heat that is sufficient to trigger a thermal decomposition of a polymerization initiator (e.g., peroxide initiator) contained within the monomer mixture 304, resulting in a polymerization reaction that forms the cross-linked material 324.

For illustrative purposes, assuming a 2 weight percent loading of heat generating microcapsules in 30 g of self-healing polymeric matrix material (having monomer mixture microcapsules dispersed therein) yields 0.6 g of the heat generating microcapsules. In this example, to achieve a suitable stoichiometry, 57% of the multiple-compartment microcapsules are loaded with finely divided iron powder; 43% with an oxidizer yielding 0.342 g Fe. Based on the exothermic reaction of iron and oxygen previously described herein, 250 grams of Fe would yield 1841 kJ, and oxidation of this mass of iron particles liberates 2.518 kJ. As an approximation, 30 grams (0.03 kg) of the self-healing polymeric matrix material (having monomer mixture microcapsules dispersed therein) may require 0.03 kJ to raise its temperature by 1° C. (1.00 kJ/kg C*0.03 kg=0.03 kJ/C). Assuming that the heat capacity of the self-healing polymeric matrix material (having monomer mixture microcapsules dispersed therein) is equivalent to the heat capacity of an epoxy cast resin, the heat of reaction in this example would be sufficient to raise the temperature of the 30 g of the self-healing polymeric matrix material (having monomer mixture microcapsules dispersed therein) by about 84° C. (2.518 kJ/0.03 kJ/C=83.9° C.). Depending on the desired temperature increase, the loading level and/or stoichiometry may be adjusted accordingly.

Thus, FIGS. 3A-3C illustrate an example in which a crack is formed in a self-healing polymeric matrix material (FIG. 3A), propagation of the crack results in rupture of a monomer mixture microcapsule to fill the crack with the monomer mixture (FIG. 3B), and further propagation of the crack results in application of a compressive force to a heat generating microcapsule that causes an exothermic chemical reaction which generates sufficient heat to trigger a polymerization reaction to form a cross-linked material to seal the crack (FIG. 3C).

Figure 4:
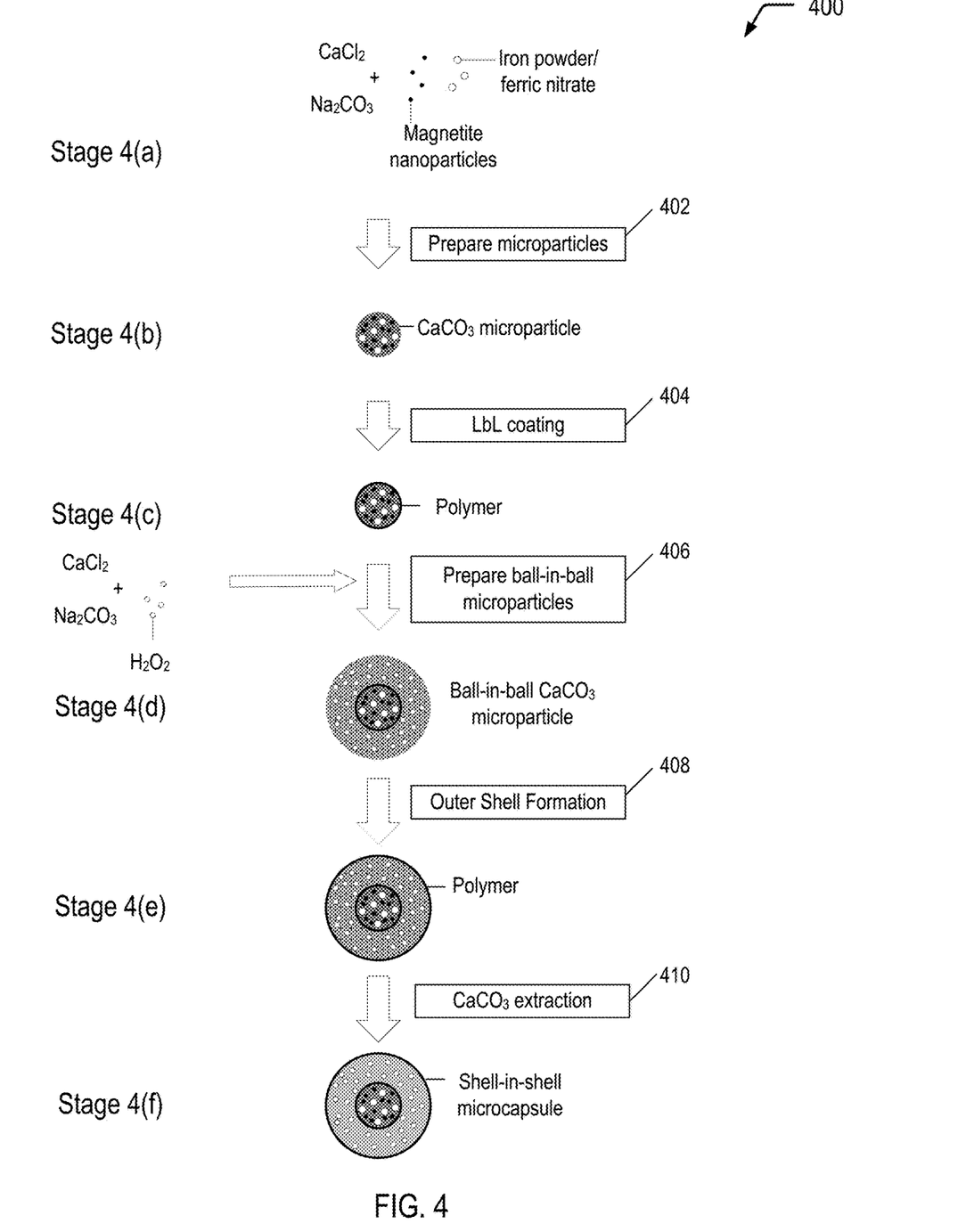
FIG. 4 is a flow diagram illustrating a method of producing a multiple-compartment microcapsule having a shell-in-shell architecture with an inner shell contained within an outer shell, where the inner shell is adapted to rupture in response to application of a compressive force to cause an exothermic chemical reaction within the microcapsule, according to some embodiments.

FIG. 4 is a flow diagram illustrating, through stages 4(a) to 4(f), an example of a method 400 of producing a multiple-compartment microcapsule having a shell-in-shell architecture with an inner shell contained within an outer shell, where the inner shell is adapted to rupture in response to application of a compressive force to cause an exothermic chemical reaction within the microcapsule, according to some embodiments. In each of the stages 4(a)-4(f), the structure is shown in a cross-sectional side view. The microcapsule produced in FIG. 4 may correspond to the multiple-compartment microcapsule 202 depicted in FIG. 2A that represents one of the heat generating microcapsules 102 depicted in FIG. 1.

In the example depicted in FIG. 4, magnetic nanoparticles are used in operation 402 for incorporation into the "inner core" $CaCO_3$ microparticles (shown at stage 4(b)). Magnetic nanoparticles are incorporated into the "inner core" $CaCO_3$ microparticles for the purpose of subsequently magnetically isolating the product prepared in operation 406 (i.e., ball-in-ball $CaCO_3$ microparticles) from a coproduct (i.e., single core $CaCO_3$ microparticles). The magnetic nanoparticles may be, for example, $Fe_3O_4$ (also referred to as "magnetite") nanoparticles, cobalt ferrite nanoparticles or other magnetic nanoparticles known in the art. In a particular embodiment, the magnetic nanoparticles may have a diameter in a range of approximately 6 nm to 25 nm.

An example of a technique of preparing magnetite nanoparticles follows. A 5 mol/l NaOH solution is added into a mixed solution of 0.25 mol/l ferrous chloride and 0.5 mol/l ferric chloride (molar ratio 1:2) until obtaining pH 11 at room temperature. The slurry is washed repeatedly with distilled water. Then, the resulting magnetite nanoparticles are magnetically separated from the supernatant and redispersed in aqueous solution at least three times, until obtaining pH 7. A typical average diameter of the resulting magnetite nanoparticles may be about 12 nm.

The microparticle system described with respect to FIG. 4 is based on $CaCO_3$ microparticles that are hardened by formation of a polyelectrolyte multilayer around the $CaCO_3$ microparticles. The method 400 begins by preparing spherical calcium carbonate microparticles in which finely powdered iron and magnetite nanoparticles are immobilized by coprecipitation (operation 402). Optionally, a catalyst such as ferric nitrate may be immobilized in the spherical calcium carbonate microcapsules as well as the iron powder and the magnetite nanoparticles. For example, 1 M $CaCl_2$ (0.615 mL), 1 M $Na_2CO_3$ (0.615 mL), 1.4% (w/v) magnetite nanoparticle suspension (50 µL), and deionized water (2.450 mL) containing finely powdered iron (2 mg) and, optionally, $Fe(NO_3)_3$ (0.01 mg) may be rapidly mixed and thoroughly agitated on a magnetic stirrer for about 20 seconds at about room temperature. After the agitation, the precipitate may be separated from the supernatant by centrifugation and washed three times with water. One of the resulting $CaCO_3$ microparticles is shown at stage 4(b).

The diameter of the $CaCO_3$ microparticles produced with a reaction time of 20 seconds is about 4 µm to about 6 µm. Smaller $CaCO_3$ microparticles are produced if the reaction time is reduced from about 20 seconds to about several seconds. One skilled in the art will appreciate that other metals may be used in lieu of, or in addition to, the iron powder. For example, magnesium or magnesium-iron alloy may also be used. One skilled in the art will appreciate that other magnetic nanoparticles may be used in lieu of, or in addition to, the magnetite. For example, cobalt ferrite nanoparticles may also be used. As noted above, the iron powder may be mixed with a catalyst such as ferric nitrate, which when in contact with the hydrogen peroxide (to be encapsulated in the outer shell) liberates oxygen to react exothermically with the iron powder. One skilled in the art will appreciate that other catalysts may be used in lieu of, or in addition to, the ferric nitrate. For example, sodium iodide (NaI) may also be used.

In this example, the fabrication of polyelectrolyte capsules is based on the layer-by-layer (LbL) self-assembly of polyelectrolyte thin films. Such polyelectrolyte capsules are fabricated by the consecutive adsorption of alternating layer of positively and negatively charged polyelectrolytes onto sacrificial colloidal templates. Calcium carbonate is but one example of a sacrificial colloidal template. One skilled in the art will appreciate that other templates may be used in lieu of, or in addition to, calcium carbonate.

The method 400 continues by LbL coating the $CaCO_3$ microparticles (operation 404). In operation 404, a polyelectrolyte multilayer (PEM) build-up may be employed by adsorbing five bilayers of negative PSS (poly(sodium 4-styrenesulfonate); Mw=70 kDa) and positive PAH (poly(allylamine hydrochloride); Mw=70 kDa) (2 mg/mL in 0.5 M NaCl) by using the layer-by-layer assembly protocol. For example, the $CaCO_3$ microparticles produced in operation 402 may be dispersed in a 0.5 M NaCl solution with 2 mg/mL PSS (i.e., polyanion) and shaken continuously for 10 min. The excess polyanion may be removed by centrifugation and washing with deionized water. Then, 1 mL of 0.5 M NaCl solution containing 2 mg/mL PAH (i.e., polycation) may be added and shaken continuously for 10 min. The excess polycation may be removed by centrifugation and washing with deionized water. This deposition process of oppositely charged polyelectrolyte may be repeated five times and, consequently, five PSS/PAH bilayers are deposited on the surface of the $CaCO_3$ microparticles. One of the resulting polymer coated $CaCO_3$ microparticles is shown at stage 4(c).

The thickness of this "inner shell" polyelectrolyte multilayer may be varied by changing the number of bilayers. In some cases, it may be desirable for the inner shell to rupture while the outer shell remains intact. Typically, for a given shell diameter, thinner shells rupture more readily than thicker shells. Hence, in accordance with some embodiments of the present disclosure, the inner shell is made relatively thin compared to the outer shell. On the other hand, the inner shell must not be so thin as to rupture prematurely.

The method 400 continues by preparing ball-in-ball calcium carbonate microparticles in which hydrogen peroxide is immobilized by a second coprecipitation (operation 406). "Immobilize" means "removing from general circulation, for example by enclosing in a capsule." The ball-in-ball $CaCO_3$ microparticles are characterized by a polyelectrolyte multilayer that is sandwiched between two calcium carbonate compartments. In operation 406, the polymer coated $CaCO_3$ microparticles may be resuspended in 1M $CaCl_2$ (0.615 mL), 1M $Na_2CO_3$ (0.615 mL), and deionized water (2.500 mL) containing hydrogen peroxide (1 mg), rapidly mixed and thoroughly agitated on a magnetic stirrer for about 20 seconds at about room temperature. After the agitation, the precipitate may be separated from the supernatant by centrifugation and washed three times with water. The second coprecipitation is accompanied by formation of a coproduct, i.e., single core $CaCO_3$ microparticles that contain only hydrogen peroxide. Hence, the resulting precipitate represents a mixture of ball-in-ball $CaCO_3$ microparticles and single core $CaCO_3$ microparticles. The ball-in-ball $CaCO_3$ microparticles, which are magnetic due to the immobilized magnetite nanoparticles in the inner compartment, may be isolated by applying an external magnetic field to the sample while all of the nonmagnetic single core $CaCO_3$ microparticles are removed by a few washing steps. One of the resulting ball-in-ball $CaCO_3$ microparticles is shown at stage 4(d).

The method 400 continues by LbL coating the ball-in-ball $CaCO_3$ microparticles (operation 408). In operation 408, a polyelectrolyte multilayer (PEM) build-up may be employed by adsorbing five bilayers of negative PSS (poly (sodium 4-styrenesulfonate); Mw=70 kDa) and positive PAH (poly(allylamine hydrochloride); Mw=70 kDa) (2 mg/mL in 0.5 M NaCl) by using the layer-by-layer assembly protocol. For example, the ball-in-ball $CaCO_3$ microparticles produced in operation 406 may be dispersed in a 0.5 M NaCl solution with 2 mg/mL PSS (i.e., polyanion) and shaken continuously for 10 min. The excess polyanion may be removed by centrifugation and washing with deionized water. Then, 1 mL of 0.5 M NaCl solution containing 2 mg/mL PAH (i.e., polycation) may be added and shaken continuously for 10 min. The excess polycation may be removed by centrifugation and washing with deionized water. This deposition process of oppositely charged polyelectrolyte may be repeated five times and, consequently, five PSS/PAH bilayers are deposited on the surface of the ball-in-ball $CaCO_3$ microparticles. One of the resulting polymer coated ball-in-ball $CaCO_3$ microparticles is shown at stage 4(e).

The thickness of this "outer shell" polyelectrolyte multilayer may be varied by changing the number of bilayers. Generally, it is desirable for the inner shell to rupture while the outer shell remains intact so that the reactants and the reaction products do not contaminate the material into which the multi-compartment microcapsule is dispersed. Typically, for a given shell diameter, thinner shells rupture more readily than thicker shells. Hence, in accordance with some embodiments of the present disclosure, the outer shell is made relatively thick compared to the inner shell.

Operation 410 is a $CaCO_3$ extraction. In operation 410, the $CaCO_3$ core of the ball-in-ball $CaCO_3$ microparticles may be removed by complexation with ethylenediaminetetraacetic acid (EDTA) (0.2 M, pH 7.5) leading to formation of shell-in-shell microcapsules. For example, the ball-in-ball $CaCO_3$ microparticles produced in operation 408 may be dispersed in 10 mL of the EDTA solution (0.2 M, pH 7.5) and shaken for about 4 h, followed by centrifugation and re-dispersion in fresh EDTA solution. This core-removing process may be repeated several times to completely remove the $CaCO_3$ core. The size of the resulting shell-in-shell microcapsules ranges from about 8 μm to about 10 μm, and the inner core diameter ranges from about 3 μm to about 5 μm. One of the resulting shell-in-shell microcapsules is shown at stage 4(f). Depending on the application of use, the shell-in-shell microcapsule can have a range of about 0.5 μm to about 200 μm.

As noted above, the fabrication of polyelectrolyte capsules in the method 400 of FIG. 4 is based on the layer-by-layer (LbL) self-assembly of polyelectrolyte thin films. One skilled in the art will appreciate that a multi-compartment microcapsule for heat generation in accordance with some embodiments of the present disclosure may be produced by other conventional multi-compartment systems, such as polymeric micelles, hybrid polymer microspheres, and two-compartment vesicles.

Thus, FIG. 4 illustrates an example of a process of forming a multiple-compartment microcapsule having an inner shell adapted to rupture when exposed to a compressive force in order to trigger an exothermic chemical reaction within the microcapsule. The multiple-compartment microcapsule formed according to the process depicted in FIG. 4 may correspond to the multiple-compartment microcapsule 202 illustrated and described further herein with respect to FIG. 2A.

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. A self-healing polymeric material comprising:
a polymeric matrix material;
a plurality of monomer mixture microcapsules dispersed in the polymeric matrix material, each monomer mixture microcapsule of the plurality of monomer mixture microcapsules encapsulating a mixture of materials, the mixture comprising a monomer and a heat-triggered initiator; and
a plurality of heat generating microcapsules dispersed in the polymeric matrix material, each heat generating microcapsule of the plurality of heat generating microcapsules encapsulating at least a first reactant and a second reactant, wherein:
the first reactant and the second reactant, when mixed, will undergo an exothermic chemical reaction, the exothermic chemical reaction generating sufficient heat to cause the heat-triggered initiator to initiate a polymerization reaction, and
each heat generating microcapsule of the plurality of heat generating microcapsules comprises a first compartment housing the first reactant and a second compartment housing the second reactant.

2. The self-healing polymeric material of claim 1, wherein the polymerization reaction includes a free-radical-initiated polymerization reaction.

3. The self-healing polymeric material of claim 2, wherein the heat-triggered initiator includes a peroxide initiator.

4. The self-healing polymeric material of claim 3, wherein the peroxide initiator includes lauroyl peroxide, benzoyl peroxide, or tent-butyl peroxybenzoate.

5. The self-healing polymeric material of claim 1, wherein a crack in the polymeric matrix material causes microcapsule rupture of a monomer mixture microcapsule of the plurality of monomer mixture microcapsules, the microcapsule rupture resulting in migration of the mixture of materials into the crack.

6. The self-healing polymeric material of claim 5, wherein further propagation of the crack in the polymeric matrix material results in application of a compressive force to a heat generating microcapsule of the plurality of heat generating microcapsules, the compressive force triggering the exothermic chemical reaction within the heat generating microcapsule.

7. The self-healing polymeric material of claim 6, wherein the exothermic chemical reaction within the heat generating microcapsule generates heat that triggers polymerization of the monomer that migrated into the crack to form a cross-linked material that seals the crack.

* * * * *